United States Patent [19]

Kelly et al.

[11] 4,041,955
[45] Aug. 16, 1977

[54] IMPLANTABLE LIVING TISSUE STIMULATOR WITH AN IMPROVED HERMETIC METAL CONTAINER

[75] Inventors: Frank L. Kelly, Granada Hills; Jozef I. Kie Sioe Tan, Sylmar, both of Calif.

[73] Assignee: Pacesetter Systems Inc., Sylmar, Calif.

[21] Appl. No.: 653,464

[22] Filed: Jan. 29, 1976

[51] Int. Cl.² ............................................. A61N 1/36
[52] U.S. Cl. ........................... 128/419 P; 128/419 PS
[58] Field of Search ....... 128/419 P, 419 PG, 419 PS, 128/421, 422, 423

[56] References Cited

U.S. PATENT DOCUMENTS 3,357,434  12/1967  Abell .............................. 128/419 PG
3,888,260   6/1975  Fischell ........................... 128/419 PS Primary Examiner—William E. Kamm
Attorney, Agent, or Firm—Lindenberg, Freilich

[57] ABSTRACT

An implantable hermetically sealed living tissue stimulator which includes a coil in which current is induced by an external alternating magnetic field is disclosed. All the stimulator circuit components except for one or more electrode leads are hermetically sealed within a hermetic container formed of a biocompatible metal of a thickness T, and having an electrical resistivity $\rho$, where $T/\rho \leq 0.03$, T being in mils and $\rho$ in microhm-cm. The metal thickness T is not more than 5 mils and preferably not more than 3 mils, and the electrical resistivity $\rho$ is not less than 75 microhm-cm and preferably not less than 100 microhm-cm, in order to reduce the portion of power induced in the stimulator by the magnetic field which is dissipated as heat in the hermetic metal container and to increase the portion of the induced power which penetrates the container and induces the current in the coil.

15 Claims, 4 Drawing Figures

IMPLANTABLE LIVING TISSUE STIMULATOR WITH AN IMPROVED HERMETIC METAL CONTAINER

BACKGROUND OF THE INVENTION

1. Field of the Invention

The present invention generally relates to a living tissue stimulator and, more particularly, to an improved hermetically sealed implantable living tissue stimulator.

2. Description of the Prior Art

Presently various stimulators are available commercially for providing stimulating pulses to various living tissue. Among the most widely known is the cardiac pacemaker which is used to provide stimulating pulses to a patient's heart in order to regulate the heart beat. In U.S. Pat. No. 3,867,950 issued on Feb. 25, 1975, a rechargeable cardiac pacemaker which is implantable in a body is disclosed. The advantage of such a pacemaker is that its source of power, typically a battery, can be recharged by an external alternating magnetic field, so that the pacemaker does not have to be removed periodically from the body for battery replacement, thus eliminating the need for frequent surgical operations.

As is appreciated, the body saline fluid is electrically conductive. In addition, it tends to impregnate encapsulating material, e.g., epoxy which is often used to encapsulate the components of an implantable pacemaker. Body fluid, when coming in contact with the pacemaker components tends to corrode and electrically short the components, thereby affecting the operation of the pacemaker. This problem was overcome in the prior art by sealing the pacemaker components, including the pulse generating circuitry, the battery and the recharging circuitry in a hermetic metal container which is impervious to the body fluid. The metal container is typically formed of a biocompatible metal of a thickness on the order of 10 mils (1 mil = 0.001 inch) or more.

Although the prior art hermetically sealed rechargeable pacemaker operates quite satisfactorily, it has significant disadvantages. From experiments therewith it was found that only a very small portion of the power induced in the pacemaker by the external alternating magnetic field is actually converted into useful battery charging power. Most of the induced power is dissipated as heat, particularly in heating up the hermetic metal container. This is undesirable for several reasons. Since the portion of the total induced power converted into useful battery charging power is very low the battery has to be charged more frequently and for longer periods of time than would have been the case if the charging efficiency were greater. Also, since the metal container heats up it may cause patient discomfort and/or damage to body tissue, unless the heating is controlled.

It is realized that the power actually converted to useful battery power may be increased by increasing the intensity of the external alternating magnetic field to increase the total power induced in the stimulator. However, such increase will further increase the heat dissipated by the metal container, which is most undesirable. Thus, a need exists for an improved implantable hermetically sealed pacemaker which is rechargeable by an external alternating magnetic field at a higher efficiency than hereinbefore attained. Also a need exists for an improved implantable hermetically sealed pacemaker in which the container heating due to an external alternating magnetic field is held to a minimum.

OBJECTS AND SUMMARY OF THE INVENTION

It is a primary object of the present invention to provide an improved implantable rechargeable hermetically sealed living tissue stimulator.

Another object is to provide a new implantable rechargeable living tissue stimulator which is sealed by a hermetic container and in which a significant portion of the power induced by an external alternating magnetic field is converted into useful power.

A further object of the invention is to provide a new metal container for hermetically sealing the components of an implantable rechargeable living tissue stimulator from body fluid whereby a significant portion of the power induced by an external alternating magnetic field is converted into useful power, with the new metal container being subjected to less heating than hereinbefore attainable.

Yet a further object of the invention is to provide an improved implantable living tissue stimulator which is hermetically sealed in a novel metal container characterized in that it is subjected to less heating due to the presence of an external alternating magnetic field.

These and other objects of the present invention are achieved by surrounding all the components of an implantable rechargeable living tissue stimulator with a very thin film of a biocompatible metal of high electrical resistivity and of a thickness preferably on the order of not more than 3 mils. The very thin metal film is impervious to body fluid and thus serves as a hermetic container in which all the stimulator components are hermetically sealed from coming in contact with the body fluid.

The novel features of the invention are set forth with particularity in the appended claims. The invention will best be understood from the following description when read in conjunction with the accompanying drawings.

DESCRIPTION OF THE PREFERRED EMBODIMENTS

The disadvantages of prior art living tissue stimulators and the advantages provided by the present invention will be described in connection with a cardiac pacemaker. From the following description it will become clear that the invention is not intended to be limited to cardiac pacemakers only and is applicable for use with or forming part of any implantable living tissue stimulator.

Figure 1:
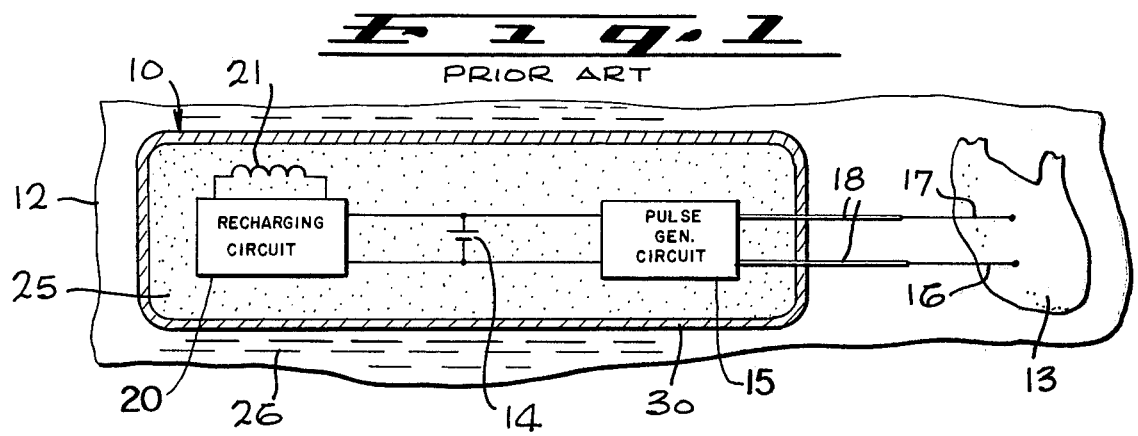
FIG. 1 is a simplified combination block and crosssectional diagram of a prior art implantable rechargeable living tissue stimulator.

FIG. 1 to which attention is directed is a simplified diagram of a prior art pacemaker 10 of the rechargeable type, which is shown implanted in a living body represented by 12, that requires stimulation of the heart 13. The pacemaker 10 typically includes a power source, e.g., a battery 14, which powers a pulse generating circuit 15 to energize electrodes 16 and 17, which extend into the heart 13 via electrode leads 18. The pulses generated by pulse generating circuitry 15 are impressed across electrodes 16 and 17.

The pacemaker 10, shown in FIG. 1, is assumed to include a recharging circuit 20, used to recharge the battery 14. The circuit 20 includes a pickup coil 21 in which currents are induced by an alternating magnetic field, provided external to the body 12. With the currents induced in the coil 21 the recharging circuitry 20 recharges the battery 14.

Typically, the pacemaker major components, i.e., the recharging circuit 20 with coil 21, the battery 14 and the pulse generating circuitry 15, hereinafter referred to as the pacemaker components, are encapsulated in encapsulating material 25. The intended function of the material 25 is to serve as electrical insulation and structural support for the pacemaker major components as well as an impervious barrier to the electrically conductive body fluid 26, which surrounds the pacemaker 10 when the latter is implanted in the body 12. Examples of the encapsulating material 25 include various resinous or plastic materials, such as epoxy, rubber compounds, waxes and the like. For explanatory purposes, it will be assumed that the encapsulating material 25 is epoxy. In U.S. Pat. No. 3,867,950 a fixed rate cardiac pacemaker of the rechargeable type is disclosed.

Although the epoxy 25 is intended to act as an impervious barrier to body fluid 25 in practice this is not the case. With the passage of time the body fluid tends to penetrate or impregnate the epoxy 25. This is most undesirable since the body fluid is electrically conductive, the body fluid is capable of providing current conductive paths for leakage currents from the pacemaker internal components to the outside of the pacemaker. Such leakage currents may present serious danger to the patient. Also the body fluid tends to corrode various electrical components thereby causing electrical malfunctioning of the pacemaker circuitry, which also represents a serious danger to the patient requiring reliable stimulation.

In order to eliminate these dangers the epoxy 25, with the pacemaker components encapsulated therein, are enclosed in a hermetic container 30, with only the electrode leads 18 extending outwardly therefrom. Typically, the container 30 is of a biocompatible metal of a thickness on the order of 10 mils or more. In one prior art embodiment, the container 30 is formed of a metal which is a wroughtable cobalt-chromium alloy with an electrical resistivity on the order of 87 microhm-cm and negligible magnetic permeability (<1.0 at 116 oersteds). It hermetically seals the pacemaker components from the electrically conductive body fluid, thereby eliminating the flow of leakage currents to or from the components via the body fluid. Also, by preventing the body fluid from reaching the pacemaker components the corrosive effect of the body fluids on the components is eliminated, thereby extending the useful life of the pacemaker.

Although such a prior art hermetically sealed pacemaker operates quite satisfactorily, it suffers from several disadvantages. The weight of the metal container 30 increases the total pacemaker weight, which is undesirable. More importantly, it has been discovered that with the prior art pacemaker when an external alternating magnetic field is applied for battery recharging only a very small portion of the total power which is induced in the pacemaker by the magnetic field is actually in the form of useful battery charging power. Most of the induced power is dissipated as heat, primarily in heating up the conventional prior art metal container 30.

Experiments were performed with a prior art rechargeable pacemaker hermetically sealed in metal container 30 formed of a wroughtable cobalt-chromium alloy of a thickness of about 10 mils. With an external alternating magnetic field which induces about 2 watts of power into such a pacemaker only about 0.06 watt is converted into useful battery charging power. About 1.8 watts are dissipated as heat in the container 30, and the remaining approximately 0.14 watt is dissipated as heat in the charging circuitry 20.

The fact that only a very small portion of the induced power is converted into useful battery charging power is most undesirable, since for proper pacemaker operation, the battery has to be recharged more frequently and for longer periods of time than would have been the case if a much greater portion of the induced power were converted into useful battery charging power. Also, the fact that most of the induced power is dissipated as heat in container 30 is very undesirable. The heat dissipated in container 30 may raise the container temperature to above body temperature, and thereby cause patient discomfort as well as present a potential source of damage to body tissue.

To overcome or reduce some of the disadvantages of the prior art it has been proposed to wind the pickup coil 21 external to the container 30 in order to increase its pick up efficiency. Namely, increase the portion of the induced power which is converted into useful battery charging power. However, a pickup coil wound external to the hermetically sealing container 30 should be shielded with a current conductive protective shield in order to prevent the flow of leakage currents to or from the coil via the body fluid. In order to further increase the pick up efficiency of coil 21 it has been proposed that it be wound about the metal container 30 and one or more slabs of a material with relatively high magnetic permeability. The intended function of the material with the high magnetic permeability is to increase the magnetic field passing through the externally wound coil and to divert the magnetic field from the metal container in order to minimize its heating. Hereafter, embodiments will be described in which the material with the high magnetic permeability will be assumed to be ferrite slabs with an assumed magnetic permeability of 100 or more and preferably 500 or more. However, it should be apparent that materials with lower magnetic permability, e.g., 10 or more, may be used. As used herein, the term "high magnetic permeability" is intended to refer to a magnetic permeability of 10 or more.

Figure 2:
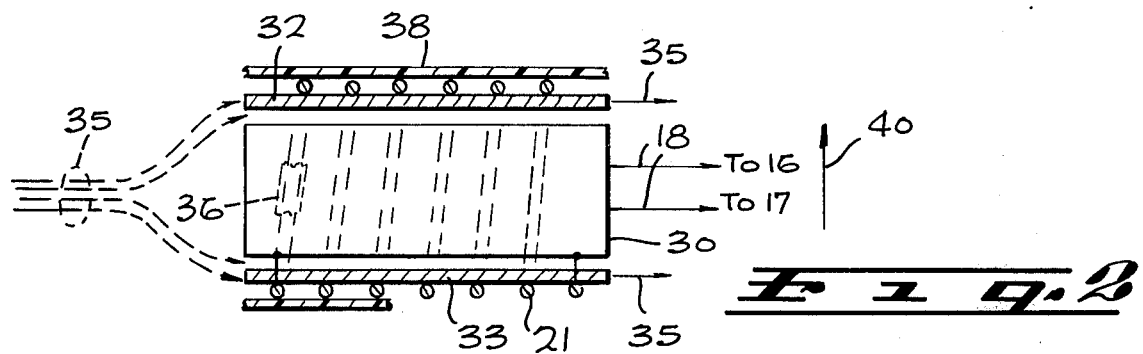
FIG. 2 is a simplified partial diagram of another embodiment of an implantable living tissue stimulator.

Embodiments of a rechargeable pacemaker with a pickup coil wound about a metal container, such as container 30, which seals all the pacemaker components except the pickup coil are described and claimed in a co-pending application, Ser. No. 653,462 filed concurrently with the present application and assigned to the same assignee. In said co-pending application an embodiment in which the pickup coil is wound around the metal hermetic container and one or more ferrite slabs is also described and claimed. FIG. 2 to which reference is now made is a simple diagram of an embodiment as described in said co-pending application. Therein, the coil 21 is shown wound about the hermetically sealing metal container 30 and two ferrite slabs 32 and 33. Lines 35 represent the external alternating magnetic field which approaches and passes through the coil 21. Numeral 36 designates a current conductive protective shield surrounding coil 21. Its function is to protect leakage currents from flowing to or from the coil 21 which is external to container 30, via the body fluid. To simplify FIG. 2 only a small section of the shield 36 is shown since it does not form part of the present invention.

For explanatory purposes both ends of coil 21 are assumed to extend through container 30 through appropriate hermetic seals into container 30 and are connected therein to the recharging circuitry 20. Sinch coil 21 is wound outside the hermetic container 30 it must be of a biocompatible metal which is resistant to corrosion by the body fluid. It is believed that in some cases it may be desirable to encapsulate the entire pacemaker circuitry, including the externally wound shielded coil 21, with a layer 38 of a biocompatible material, e.g., polyethylene of a thickness on the order of 20 mils or more to provide a smooth uniform biocompatible surface. To simplify FIG. 2 only a small portion of layer 38 is shown.

The rechargeable hermetically sealed pacemaker, as shown in FIG. 2, provides some significant advantages over prior art rechargeable hermetically sealed pacemakers, such as increased coil pick up efficiency and reduced metal container heating. However, its weight as compared with the weight of the prior art is not reduced, since in both cases the hermetic metal container 30 which is typically of a thickness of 10 mils or more is included. Also, assuming that the direction, represented by arrow 40, designates the thickness direction of the pacemaker, since coil 21 is wound about the container 30, which is included, and since the coil 21 may be shielded by shield 36 and outer layer 38 may be included, the actual pacemaker thickness is increased.

In accordance with the present invention, an improved hermetically seald rechargeable pacemaker is provided in which a very significant portion of the power induced in the pacemaker by the magnetic field is converted into useful battery charging power, while the portion of the induced power dissipated in heating the hermetically sealing metal container is significantly smaller than in the prior art. In addition, the total weight and thickness of the pacemaker are less than a pacemaker including comparable internal components.

Figure 3:
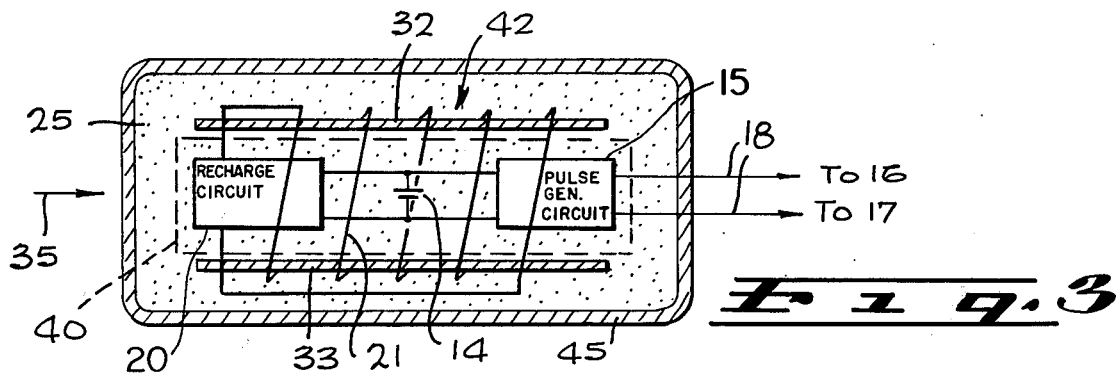
FIGS. 3 and 4 are simplified diagrams useful in explaining the present invention.

Attention is now directed to FIG. 3 which represents a simplified cross-sectional and block diagram of a preferred embodiment of the invention. In FIG. 3 elements like those previously described are designated by like numerals. In the preferred embodiment, the pacemaker internal components, such as recharging circuitry 20, except for coil 21, battery 14 and pulse generating circuitry 15, are assumed to be mechanically supported by a block of epoxy or other like material, represented by numeral 40. A pair of ferrite slabs 32 and 33 or other material of high magnetic permeability are placed on opposite sides of the epoxy block 40. The pickup coil 21 is wound about these slabs and the epoxy block 40, with the ends of the coil being connected to recharging circuitry 20.

Thereafter, the coil 21, with the slabs 32 and 33 and the epoxy block 40 are covered with a layer of epoxy 25. This layer effectively defines a block of epoxy, designated by 42, which is greater than block 40 and, which in addition to encapsulating the latter, also encapsulates coil 21 and slabs 32 and 33. Thereafter, the epoxy block 42 is hermetically sealed within a metal container 45, with only electrode leads 18 extending therefrom. Container 45 is formed of a very thin layer or film of a biocompatible metal of a thickness, preferably on the order of not more than 3 mils. Also, the biocompatible metal is one having a high electrical resistivity, and very low magnetic permeability.

It should be pointed out that unlike the arrangement shown in FIG. 2, in which only the recharging circuitry 20, the battery 14 and the pulse generating circuitry 15 are assumed to be hermetically sealed in the relatively thick (about 10 mils) metal container 30, while the coil 21 and the slabs are outside the container 30 in the preferred embodiment of the pacemaker of the present invention, as shown in FIG. 3, all the pacemaker parts are hermetically sealed in container 45. Thus, the current conductive protective shield 36 around coil 21 is not required. Furthermore, the coil can be formed from any low resistance metal, e.g., such as copper and is not limited to the few metals which are both biocompatible and corrosion resistant, and generally exhibit higher resistivity. Thus, a thinner and lighter wire can be used in forming coil 21. Also, the outer layer 38 is not needed. Since the container 45 is formed of a very thin metal film and serves as a hermetic container for all the pacemaker parts it may be referred to hereinafter as the thin metal film hermetic container.

Since the container 45 hermetically seals all the pacemaker parts it eliminates the need for the much heavier metal container 30, the coil shield 36, layer 38, and furthermore enables the formation of coil 21 from thinner and lighter wire. And, since it is formed of a very thin metal film it reduces significantly the weight and size of the pacemaker, as compared with the pacemaker embodiment as shown in FIG. 2.

It is recognized that in the embodiment of the pacemaker of the present invention the external alternating magnetic field 35 has to pass to coil 21 through the container 45. It has been discovered however that as long as container 45 is formed of a thin film of not more than 5 mils and preferably on the order of 3 mils or less of a biocompatible metal of relatively high resistivity, e.g., on the order of 75 microhm-cm or more and very low magnetic permeability, the pick up efficiency of the enclosed coil 21 is very high. Consequently, the battery charging frequency and charging periods can be reduced significantly. Furthermore, with such a container the portion of the power induced by the magnetic field in the form of heating the container is relatively small.

As previously mentioned it has been found that when about 2 watts are induced by the magnetic field in a prior art pacemaker, such as that shown in FIG. 1 in which the coil 21 is hermetically sealed in container 30 which is a wroughtable cobalt-chromium alloy of a thickness of about 10 mils only 0.06 watt is converted into useful battery charging power, while about 1.8 watts representing about 90% of the total induced power is dissipated in the form of heat in the container 30. About 0.14 watt is dissipated as heat in the electrical components. It has been discovered that by replacing such a prior art container 30 with container 45 formed of a thin film of not more than 3 mils of titanium 6-4, with comparable induced power by the magnetic field of about 2 watts, about 0.9 watt is converted into useful battery charging power and only about 35% of the total induced power or about 0.7 watt is dissipated in heating container 45. The rest of the induced power is dissipated as heat in the electrical components. Titanium 6-4 is a titanium alloy with an electrical resistivity of about 170 microhm-cm and a very low magnetic permeability, e.g., about 1 at 20 oersteds.

From the foregoing it should thus be appreciated that the thin metal film hermetic container 45 provides significant advantages when used to hermetically seal components of a pacemaker which is rechargeable by an external alternating magnetic field. A smaller portion of the power induced in the pacemaker by the magnetic field is dissipated as heat in the container as compared with the heat dissipated in the prior art container 30 by a magnetic field inducing the same amount of power. Consequently, more of the magnetic field power penetrates the container 45 thereby significantly increasing the portion of the induced power which is convertable by the pickup coil and the recharging circuitry 20 into useful battery charging power. Since less power is dissipatrd as heat in the container 45, its temperature increase is much less than that experienced in the prior art container 30. Thus, the likelihood of patient discomfort and/or damage to body tissue due to the heated container are greatly reduced.

Prior to actually constructing the thin metal film hermetic container 45 it was believed that a metal film of about 3 mils thick or less will not provide the required mechanical strength. However, actual experiments have proven that when the metal film is formed around the epoxy block 42, the latter provides sufficient support for the thin metal film in order to act as a hermetically sealing thin metal film container of sufficient mechanical strength.

Figure 4:
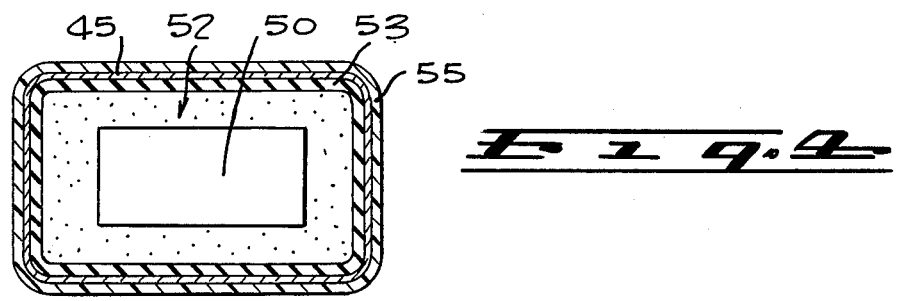

The present invention is not intended to be directed solely to a container formed of a very thin metal film around a block of encapsulating matter such as epoxy block 42, as shown in FIG. 3. If desired all the pacemaker components may be enclosed in a hollow inner container, formed of a thin layer of encapsulating type material, such as epoxy, rubber compounds or the like, with the thin metal film layer forming container 45 completely surrounding the inner container. Such an arrangement is shown in FIG. 4. Therein, numeral 50 is assumed to designate all the pacemaker major components. The inner container is designated by numeral 52 and is assumed to be formed of a layer 53 of encapsulating type material surrounded by the thin metal film hermetic container 45. Layer 53 should be sufficiently thick, e.g., 20 mils or more in order to provide sufficient mechanical strength to the overlying thin metal film forming container 45.

In order to realize the advantages of the present invention the hermetic container should be formed of a thin layer or film of metal which is impervious to both body fluid and gases. The metal thickness should be in the low mil range, namely not more than 5 mils and preferably not more than 3 mils. It should be of a metal with high electrical resistivity of not less than 75 microhm-cm and preferably not less than 100 microhm-cm. The metal should be of the biocompatible type since it will come in contact with body fluid. In general for optimum results the relationship between the thickness and electrical resistivity of the biocompatible metal used to form the hermetic container in accordance with the present invention may be expressed by the following expression:

$$T/\rho \leq 0.03$$

where T is the metal thickness in mils and $\rho$ is the metal electrical resistivity in microhm-cm.

In the event the heat which is dissipated in the container 45 tends to concentrate at localized spots, sometimes referred to as "hot spots", the thin metal film, forming container 45, may be coated with an outer thin layer of heat-insulating material, designated in FIG. 4 by numeral 55. Such a layer of a thickness of 10–20 mils or more will serve to distribute any concentrated heating of container 45 at one or more hot spots over a larger surface area and thereby further reduce any likelihood of patient discomfort or damage to body tissue. Examples of materials from which layer 55 may be formed include implantable medical grade plastics like silicone rubber, polyethylene, polyprophylene and the like. All such materials, in addition to having very low thermal conductivity, also have very high electrical resistivity, at least 100 times greater than that of the metal container 45.

Hereinbefore titanium 6-4 has been mentioned as one example of a metal from which container 45 may be formed. It is characterized by a resistivity of about 171 microhm-cm and very low magnetic permeability. Examples of some other metals which may be used to form container 45 include titanium 3-2-5 which is a titanium alloy, with an electrical resistivity of 126 microhm-cm, a wroughtable cobalt-chromium alloy with an electrical resistivity of about 88 microhm-cm, 316L stainless steel with an electrical resistivity of 74 microhm-cm, and a multiphase nickel alloy, known as MP35N with an electrical resistivity of 101 microhm-cm. All of these metals have low magnetic permeability.

It should be appreciated that various known techniques may be used to form the thin metal film hermetic container 45. It may be formed from shallow drawn thin metal foil, with seams welded, such as by electron or seam beam welding techniques to form the hermetic container. Also, the thin metal film may be deposited or electroplated on the epoxy block 42 to form container 45. Clearly, the method employed may to some degree control the metal which is selected.

It should be pointed out that the present invention provides advantages when used to hermetically seal the parts of any implantable pacemaker whether or not it is of the rechargeable type and/or one designed to respond to an external alternating magnetic signal. A patient with an implantable pacemaker may be present where an external magnetic field is present, such as some RF ovens. Such a field may pass through the skin and heat the hermetically sealing container. If the container is one used in the prior art the container may become sufficiently hot to cause discomfort and possible damage to body tissue. However, when the pacemaker incorporates the novel thin metal film hermetic container of the present invention since its heating due to an external alternating magnetic field is low the possible discomfort to the patient and/or damage to body tissue are greatly reduced.

Although particular embodiments of the invention have been described and illustrated herein, it is recognized that modifications and variations may readily occur to those skilled in the art and consequently, it is intended that the claims be interpreted to cover such modifications and equivalents.

The embodiments of the invention in which an exclusive property or privilege is claimed are defined as follows:

1. In an implantable living tissue stimulator of the type including a plurality of circuit means, the improvement comprising:

hermetic means for hermetically sealing at least some of said circuit means, said hermetic means comprising a hermetic container formed of a thin layer of metal of a thickness definable as T, said metal being characterized by an electrical resistivity definable as $\rho$, where $T/\rho < 0.03$, T being in mils and $\rho$ in microhm-cm, said metal layer being impervious to body saline fluid and gases.

2. The improvement as described in claim 1 wherein the metal is a biocompatible metal of a thickness of less than 3 mils.

3. The improvement as described in claim 1 wherein the metal electrical resistivity is greater than 100 microhm-cm.

4. The improvement as described in claim 1 wherein said metal has an electrical resistivity of substantially 170 microhm-cm and its thickness is not more than substantially 2 mils.

5. The improvement as described in claim 1 wherein said metal is a titanium alloy with an electrical resistivity of substantially 170 microhm-cm, said improvement further including a layer of material exhibiting heat-insulating properties on top of said metal, said layer of material having an electrical resistivity which is greater than that of the metal by a factor of not less than 100, and exhibiting resistance to corrosion by body saline fluid.

6. The improvement as described in claim 5 wherein the metal thickness is not greater than 3 mils.

7. The improvement as described in claim 1 wherein the metal is a biocompatible metal and the improvement further including a layer of heat insulating matter on top of said metal layer.

8. For use with a device implantable in a living body, said device including circuitry, a hermetically sealing container formed of a biocompatible metal for containing said circuitry to prevent body saline fluid from coming in contact with said circuitry, the container being formed of a metal characterized by an electrical resistivity definable as $\rho$, and of a thickness T, $T/\rho$ being not greater than 0.02, where $\rho$ is in microhm-cm and T is in mils.

9. The container as recited in claim 8 where $\rho$ is not less than 120.

10. The container as recited in claim 9 wherein the metal is of a titanium alloy.

11. The container as recited in claim 9 wherein $\rho$ is about 170 microhm-cm.

12. The container as recited in claim 9 wherein T is not greater than 3 mils and $\rho$ is about 170 microhm-cm.

13. The container as recited in claim 12 wherein T is less than 3 mils.

14. The metallic container as recited in claim 9 and including a layer of material with heat-insulating properties on said metallic container, said layer of material being characterized by an electrical resistivity which is greater than the resistivity of said metallic container by a factor of not less than 100.

15. The container as recited in claim 14 wherein the electrical resistivity of said metal container is about 170 microhm-cm and T is not greater than 3 mils.

* * * * *